United States Patent [19]

Lester

[11] 4,284,083
[45] Aug. 18, 1981

[54] INHALATION INCENTIVE DEVICE

[76] Inventor: Victor E. Lester, P.O. Box 608, Sonora, Calif. 95370

[21] Appl. No.: 42,862

[22] Filed: May 29, 1979

[51] Int. Cl.$^3$ .............................................. A61B 5/08
[52] U.S. Cl. .................................... 128/725; 128/727; 272/99
[58] Field of Search ............................... 128/725–727; 272/99

[56] References Cited

U.S. PATENT DOCUMENTS

| | | | |
|---|---|---|---|
| 3,720,202 | 3/1973 | Cleary | 128/727 |
| 3,754,546 | 8/1973 | Cooper | 128/727 |
| 3,848,584 | 11/1974 | Otsap | 128/727 |
| 3,908,987 | 9/1975 | Boehringer | 272/99 |
| 4,025,070 | 5/1977 | McGill et al. | 128/727 |
| 4,094,508 | 6/1978 | Kirsch | 128/725 |
| 4,138,105 | 2/1979 | Hunger et al. | 128/725 X |
| 4,158,360 | 6/1979 | Adams | 128/725 |
| 4,170,228 | 10/1979 | Elson et al. | 128/725 |
| 4,171,804 | 10/1979 | Thead | 128/727 X |
| 4,183,361 | 1/1980 | Russo | 128/725 |
| 4,221,381 | 9/1980 | Ericson | 128/727 |

OTHER PUBLICATIONS

*Resp. Therapy*, "Triflo II", (Chesebrough–Ponds, Inc.), Dec. 1977.

Primary Examiner—Kyle L. Howell
Attorney, Agent, or Firm—Lyon & Lyon

[57] ABSTRACT

An inhalation device for indicating inhalation flow rate and the passage of time between inhalations, including a vertical cylindrical chamber having a lower first closed end with a first one-way valve for allowing gas flow into said chamber, an upper second closed end, an outlet proximate said upper closed end for inhalation, the interior surface of the sidewalls of said chamber defining an inside horizontal cross sectional area substantially constant from said first closed end to an area intermediate said first closed end and said second closed end, said chamber sidewalls further defining a gradually increasing horizontal cross sectional area from said intermediate area to said second closed end. Disposed vertically within said vertical chamber and concentrically aligned therewith is a tubular member with a plurality of openings proximate said upper closed end, said tubular member being in communication with an inhalation exhalation outlet and a second one-way valve for exhalation. Said device further includes a horizontal indicator disc disposed within said chamber having a horizontal cross sectional area slightly less than said substantially constant horizontal cross sectional area of said chamber, said indicator disc guided vertically within said chamber by means of said tubular member.

23 Claims, 3 Drawing Figures

U.S. Patent    Aug. 18, 1981    4,284,083
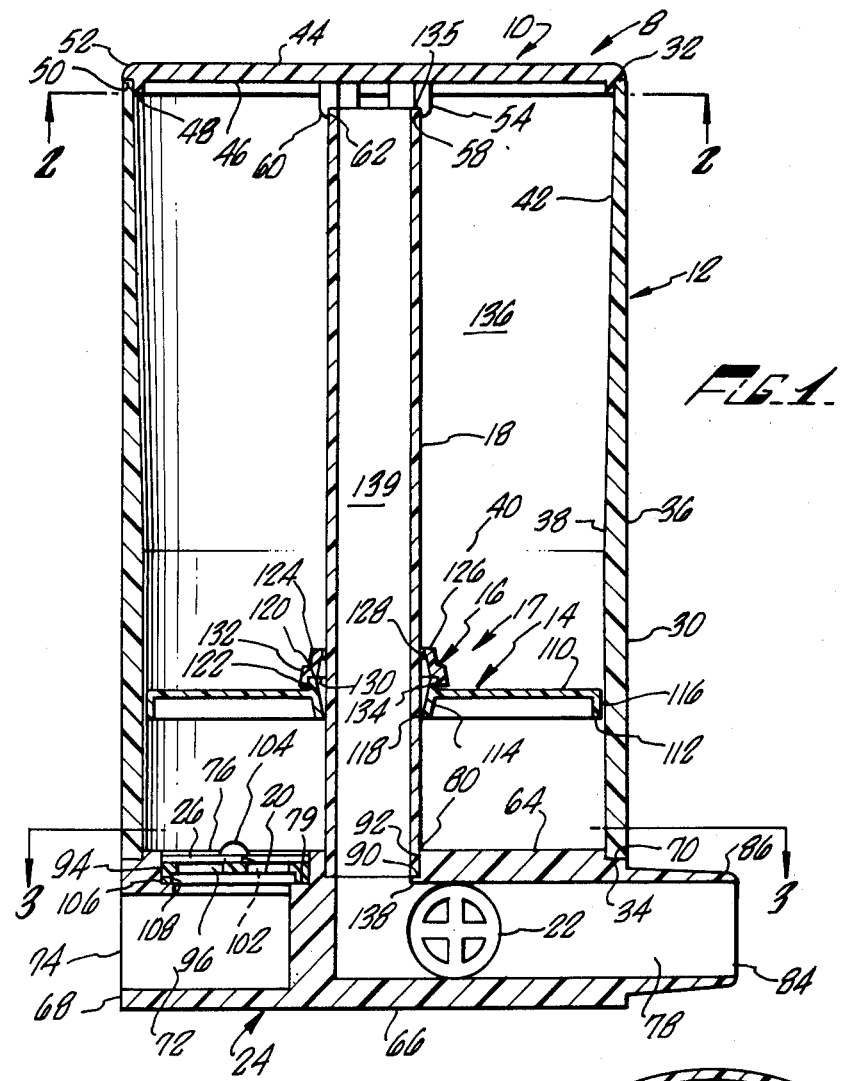
FIG. 1.
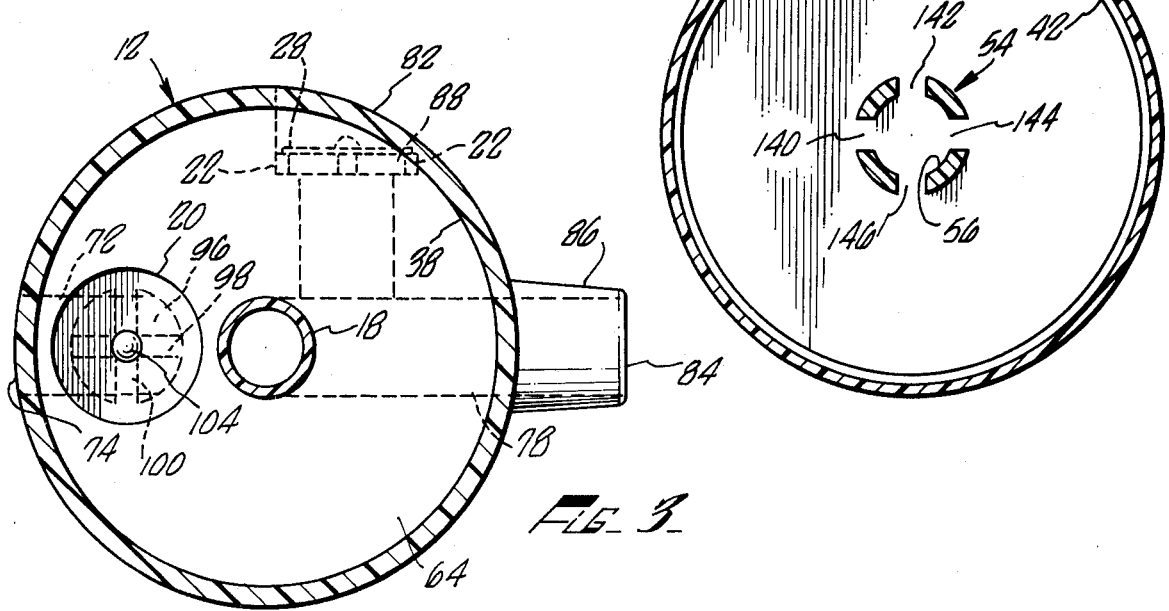
FIG. 2.
FIG. 3.

INHALATION INCENTIVE DEVICE

This invention relates to the field of inhalation therapy devices and more particularly to an inhalation monitoring device.

During the treatment of various respiratory disorders or during the rehabilitation of respiratory ability, it is often desirable to prescribe the inhalation flow rate a patient may achieve. It is also desirable to prescribe the rate of inhalations. Preferably, a visual indication of these rates should be made readily available to the patient. The principal advantage of such visual indication is that it encourages the patient and is an incentive to the patient, to breathe within prescribed rates.

A device that is known to me which is sold by Chesebrough-Pond's, Inc., under the tradename "TriFlow II" indicates inhalation flow rate only; the device gives no indication of the passage of time between inhalations. Moreover, the device positively indicates only three distinct flow rates; flow rates that are below, between or above those distinct flow rates will not be adequately indicated.

The device of the present invention overcomes the above limitations by indicating inhalation flow rate over a continuous range rather than only indicating several distinct flow rates. Additionally, the present invention indicates the passage of time from the previous inhalation. These advantages are combined in a device that a patient can easily learn to use in order to monitor his inhalation flow rate and frequency. The device is also readily manufactured and is relatively inexpensive.

The inhalation device disclosed herein generally consists of a transparent vertical cylindrical chamber that is sealed at both ends by horizontal end discs. Coaxially disposed within the cylinder is a vertical tubular member that penetrates the lower end disc and extends upwardly to an area proximate to the interior surface of the upper end disk where a plurality of openings are formed between the tubular member and the upper end disc for communication between the upper end of the chamber and the interior of the tubular member. The lower end disc is of sufficient thickness to include a first chamber that is open to the atmosphere and a first one-way valve that connects the interior of the vertical chamber with the first chamber. The lower end disc further includes a second chamber that is in communication with the interior region of the tubular member, an outlet through which the patient breathes, and a second one-way valve that vents the patient's exhalation from the outlet to the atmosphere. The interior surface of the vertical chamber sidewalls is gradually tapered from an area intermediate the lower and upper discs to gradually increase the horizontal cross sectional area of the vertical chamber from the intermediate area toward the upper end disc. Disposed concentrically within the vertical chamber is a horizontal indicator disc that is adapted to readily slide along the tubular member throughout the length of the vertical chamber. The horizontal cross sectional area of the indicator disc is slightly less than the interior horizontal cross sectional area of the vertical chamber between the lower end disc and the intermediate area.

As a patient inhales, a flow path including the first chamber, first one-way valve, vertical chamber, tubular member, second chamber and the outlet is formed. The indicator disc within the vertical chamber is drawn upwardly to an equilibrium position within the tapered portion of the vertical chamber. When the patient next exhales through the second chamber and the second one-way valve, the inhalation flow path previously established ceases, and the first one-way valve closes, establishing a gas cushion between the indicator disc and the lower end disc. The indicator disc then settles toward the lower end disc as the gas cushion slowly escapes through the annular region defined by the outer edge of the indicator disc and the inner surface of the vertical chamber. The equilibrium position achieved by the indicator disc during inhalation indicates inhalation flow rate; the change in position during the gradual settling of the indicator disk toward the lower end disk indicates the passage of time since the previous inhalation.

It is therefore an object of the present invention to provide an inhalation device that usually indicates inhalation flow rate continuously throughout a range of flow rates.

It is a further object of the present invention to provide an inhalation device that usually indicates the passage of time since a previous inhalation.

It is a further object of the present invention to provide an inhalation device which can be readily interpreted by a patient.

It is still another object of the present invention to provide an inhalation device that is easy to use and inexpensive to manufacture.

Other objects and advantages of this invention will be apparent from the following description and accompanying drawings.

FIG. 1 is a side-sectional view of the present invention.

FIG. 2 is a sectional view of the present view taken substantially through line 2—2.

FIG. 3 depicts a cross-sectional view of the device of the present invention taken substantially through line 3—3.

Referring now in detail to the drawings, a preferred embodiment of the inhalation device 8 of the present invention consists of ten separately formed components that are then assembled to form a complete device. The components include upper end disc 10, cylindrical chamber 12, indicator disc 14, retainer 16, inhalation tube 18, first one-way valve 20, second one-way valve 22, lower end disc 24, first pliable valve member 26, and second pliable valve member 28.

Cylindrical chamber 12 is formed from a generally thin vertical transparent sidewall 30 that terminates in upper annular edge 32 and lower annular edge 34. Upper annular edge 32 and lower annular edge 34 lie in horizontal planes that are perpendicular to the vertical axis of cylindrical chamber 12. Outside surface 36 of sidewall 30 is smooth and has a constant horizontal diameter from upper annular edge 32 to lower annular edge 34. Lower inside surface 38 has a substantially constant horizontal diameter from lower annular edge 34 to horizontal area 40 which is defined to be the intersection of a horizontal plane perpendicular to the vertical axis of cylindrical chamber 12 and sidewall 30, said horizontal plane lying slightly nearer lower annular edge 34 than a horizontal plane intermediate upper annular edge 32 and lower annular edge 34. Upper inside surface 42 of sidewall 30 has a horizontal inside diameter at horizontal area 40 that is equal to the horizontal inside diameter of lower inside surface 38. As upper inside surface 42 extends from horizontal area 40 to upper annular end 32, the horizontal diameter of upper inside surface 42 gradually increases forming a slightly increasing inside taper into sidewall 30 from horizontal area 40 to upper annular edge 32.

Upper end disc 10 is a generally disc-shaped member having a thin cross-section with a generally horizontal upper surface 44 and a generally horizontal lower surface 46. Formed near the outer edge of lower surface 46 and extending downwardly therefrom is annular ridge 48 which defines shoulder 50 to be co-planer with lower surface 46. One-quarter outside radius 52 perpendicularly intersects shoulder 50, forming a substantially continuous and smooth surface with upper surface 44. Protruding from lower surface 46 and generally coaxial with upper end disc 10 is segmented tubular extension 54, each segment thereof having an inside surface 56 and a horizontal shoulder surface 58 adjacent to inside surface 56, the horizontal shoulder surface 58 of each segment cooperating to define a segmented annular shoulder parallel to lower surface 46. Each segment of segmented tubular extension 54 extends beyond horizontal shoulder surface 58 to form a flange segment 60 with a flange segment inside surface 62 adjacent to horizontal shoulder surface 58.

Lower end disc 24 has a generally disc-shaped upper surface 64 and lower surface 66 and a generally cylindrical outside surface 68. Formed into the outer edge of upper surface 64 is annular shoulder 70 which is adapted to receive lower annular edge 34 of sidewall 30, annular shoulder 70 lying in a horizontal plane that is perpendicular to the central vertical axis of lower end disc 24. Formed between outside surface 68 and upper surface 64 is first chamber 72 connecting opening 74 at outside surface 68 with opening 76 of upper surface 64. Annular shoulder 77 is formed into upper surface 64 at opening 76 to receive first one-way valve 20 as will be subsequently described.

Also formed into lower end disc 24 is second chamber 78 that connects opening 80 centrally located on upper surface 64, opening 82 formed through outer surface 68, and opening 84 at the outer extension of tubular member 86. Tubular member 86 extends from outer surface 68 generally perpendicular to a vertical central axis of lower end disc 24. The outer surface of tubular member 86 is slightly tapered to receive standard 22 mm. corrugated tubing as is well known in the art. Annular shoulder 88 is formed into opening 82 for receiving second one-way valve 22 as will be subsequently described. The central axis of opening 82 is generally perpendicular and co-planer with the central axis of tubular member 86. Annular shoulder 90 having shoulder sidewall 92 is formed into upper surface 64 at opening 80 and is adapted to receive one end of inhalation tube 18 as will be described.

First one-way valve 20 and second one-way valve 22 are identical and each comprise a disc 94 into which a plurality of openings 96 are formed, said openings defining perpendicularly intersecting cross-members 98 and 100. Stem 102, located at the intersection of crossmembers 98 and 100, protrudes from a first surface of disc 94 to support head 104 which is formed to include a first flat surface substantially parallel to said first surface of disc 94 and spaced from said surface to allow for a thickness of first pliable valve member 26. A second rounded surface of head 104 extends away from the first surface of disc 94 to aid in mounting first pliable valve member 26. Flange 106 is formed at the outer edge of a second surface of disc 94, flange 106 defining an annular surface 108 in a plane parallel to the second surface of disc 94.

Indicator disc 14 comprises a disc member 110, a cylindrical outer edge member 112, and a frustum conical bearing member 114. The outer edge surface of disc member 110 and the outer surface of cylindrical outer edge 112 cooperate to define outer cylindrical surface 116, the diameter of which is slightly less than the inside horizontal diameter of lower inside surface 38. Bearing member 114 is centrally formed into disc member 110 and has a tapered inside surface that terminates in circular bearing edge 118. The diameter of bearing edge 118 is adapted to receive and freely slide over the outside surface of inhalation tube 18 as will be described. The upper end of bearing member 114 defines a coaxial annular end surface 120 and an outside expanding tapered surface 122.

Retainer 16 has a frustum conical sidewall 124 that terminates at its upper end in annular flange 126, defining circular opening 128. The diameter of circular opening 128 is adapted to receive and freely slide over the outside surface of inhalation tube 18, the purpose of which will be made apparent. The lower end of sidewall 124 forms annular flat bonding surface 130 and expands to form lip 132 with inside tapered surface 134 that is coaxial with opening 128. Indicator disc 14 and retainer 16 are bonded together to form indicator member 17 with end surface 120 abuting surface 130 and outside expanding tapered surface 122 abuting inside tapered surface 134. When bonded together in this fashion, opening 128 is positioned to be coaxial with circular bearing edge 118.

Inhalation tube 18 has a hollow cylindrical cross-section and includes a first and upper end surface 135 and a second and lower end surface 138. The outside diameter of inhalation tube 18 is adapted to be received by each flange segment 60 of segmented tubular extension 54 and is further adapted to be received by opening 80 and shoulder sidewall 92.

First and second pliable valve members 26 and 28 are preferably formed from a disc of pliable materials such as sheet rubber. A hole is formed and to the center of first pliable valve member 26 of sufficient diameter to fit around stem 102 but to be retained between the first surface of disc 94 and the flat surface of head 104. A similar hole is formed into second pliable valve member 28 so as to be retained by a similar stem and head of second one-way valve 22.

To form a complete inhalation monitoring device 8, first pliable valve member 26 is forced over head 104 to retain first pliable valve member 26 against a first surface of disc 94. Second pliable valve member 28 is similarly attached to second one-way valve 22. First one-way valve 20 is then pressed into opening 76 such that annular surface 108 abuts shoulder 78 and the outer edges of disc 94 and flange 106 abut the inside surface of opening 76. Second one-way valve 22 is similarly pressed into opening 82 to abut annular shoulder 88. As illustrated in FIG. 1, lower annular edge 34 of cylindrical chamber 12 is bonded to annular shoulder 70 of lower end disc 24, coaxially aligning cylindrical chamber 12 with the central axis of lower end disc 24. Inhalation tube 18 is pressed into opening 80 such that lower end surface 138 abuts annular shoulder 90. Indicator member 17 described above is disposed over the outer surface of inhalation tube 18, this outer surface and opening 128 of retainer 16 along with circular bearing edge 118 of indicator disc 14 forming a bearing that guides indicator member 17 along inhalation tube 18. Upper end disc 10 is bonded to cylindrical chamber 12 to define vertical chamber area 136 between lower surface 46 of upper end disc 10 and upper surface 64 of lower end disc 24. Upper annular edge 32 of sidewall 30 abuts shoulder 50 of upper disc 10 and the outer surface of annular ridge 48 abuts upper inside surface 42 to co-axially align upper end disc 10, cylindrical chamber 12 and lower end disc 24. The outer surface and the upper end surface 135 of inhalation tube 18 cooperate with horizontal shoulder surface 58 and flange segment inside surface 62 of each flange segment 60 that comprise segmented tubular extension 54 to retain inhalation tube 18 and to coaxially align inhalation tube 18 and indicator member 17, with upper end disc 10, cylindrical 12 and lower end disc 24. Once the inhalation device 8 is completed, upper surface 44, one-quarter outside radius 52, outside surface 36 and outside surface 68 cooperate to form a substantially smooth and continuous overall outer surface that is completed by lower surface 66 and tubular member 86.

Turning now to a description of the inhalation device 8 in use, an inhalation therapy face mask or mouthpiece through which the patient inhales and exhales is attached to tubular member 86, for example, by means of a length of standard 22 mm. corrugated hose. Initially, indicator member 17 assume an at-rest position at the lower end of chamber area 136 adjacent to upper surface 64 of lower end disc 24. As the patient begins to draw inhalation gases through second chamber 78, interior region 139 of inhalation tube 18, and chamber area 136 through openings 140, 142, 144 and 146 as defined by lower surface 46, segmented tubular extension 54 and inhalation tube 18, second pliable valve member 28 is drawn against second one-way valve 22 to close and seal the valve, and first pliable valve member 26 is drawn away from first one-way valve 20 to open first one-way valve 20, thus establishing an inhalation flow path comprising opening 74, first chamber 72, openings generally designated 96 of first one-way valve 20, chamber area 136, openings 140-146, interior region 138, and second chamber 78. The flow path upwardly through chamber area 136 from first one-way valve 20 to openings 140-146, however, is restricted by indicator member 17 which occupies a substantial cross-sectional area within lower inside surface 38. Since indicator member 17 is free to move along inhalation tube 18, indicator member 17 will be drawn upwardly toward upper end disc 10. As indicator member 17 passes through horizontal area 40, the horizontal cross-sectional area of chamber 136 that is restricted by member 17 gradually increases as defined by the taper of inside surface 42, thus gradually decreasing the tendency of indicator member 17 to be drawn upwardly by the inhalation flow through chamber area 136. Eventually, an equilibrium position will be reached by member 17 whereby the weight of indicator member 17 is equal to the upwardly urging force applied to indicator member 17 by inhalation gases flowing upwardly within chamber 136 and through an annulus formed between outer cylindrical surface 116 and upper inside surface 42. This equilibrium position of indicator member 17 will correspond to a particular inhalation flow rate; greater inhalation flow rates will cause indicator member 17 to reach an equilibrium position nearer upper end disc 10 thereby increasing the area of the annulus defined between outer cylindrical surface 116 and upper inside surface 42. Similarly, lesser inhalation flow rates will cause indicator member 17 to assume an equilibrium position nearer horizontal area 40, defining a smaller annulus between outer cylindrical surface 116 and upper inside surface 42. In this way, the equilibrium positions achieved by member 17 within chamber area 136 between upper end disc 10 and horizontal area 40 will indicate corresponding specific inhalation flow rates. The outer diameter of cylindrical surface 116 and the taper formed into upper inside surface 42 determine the range of inhalation flow rates that may be indicated.

Once the patient ceases inhalation and begins exhalation, first pliable valve member 26 is forced against first one-way valve 20 to seal that valve and second pliable valve member 28 is forced away from second one-way valve 22, thus opening second one-way valve 22 and thereby creating a path for exhalation through second chamber 78, second one-way valve 22 and opening 82. Because first one-way valve 20 is closed, no exhalation gases will flow through interior region 139, openings 140-146, and chamber area 136. Indicator member 17, now unsupported by upwardly flowing inhalation gases, will drop downwardly in chamber area 136 from an equilibrium position toward lower end disc 24. As indicator member 17 descends, it will be supported by a cushion of gas trapped within chamber area 136 between indicator member 17 and lower end disc 24; the rate of descent of indicator member 17 will be regulated by the rate at which the gas thusly trapped will be allowed to escape through the annulus defined by outer cylindrical surface 116 and upper inside surface 42 or lower inside surface 38. Thus the rate of descent of indicator member 17 will rapidly decrease as the area of the annulus defined between outer cylindrical surface 116 and upper inside surface 42 decreases. Once indicator member 17 reaches horizontal area 40, the area of the annulus defined between outer cylindrical surface 116 and lower inside surface 38 will remain constant, resulting in a constant rate of descent of indicator member 17 from horizontal area 40 toward lower end disc 24. Since the horizontal cross-sectional area of indicator member 17 occupies a substantial portion of the horizontal cross-sectional area of chamber 136 within lower inside surface 38, the resulting annulus between outer cylindrical surface 116 and lower inside surface 38 will, have a corresponding substantially small area through which the trapped gas may escape, causing indicator member 17 to descend relatively slowly toward lower end disc 24. The distance that indicator member 17 descends from horizontal area 40 toward lower end disc 24 will therefore indicate the passage of time since the last inhalation.

As the patient completes exhalation and begins inhalation, indicator member 17 will again be drawn upwardly within chamber area 136 as described above. An indication of inhalation flow rate followed by an indication of the passage of time from the previous inhalation will then be repeated for each inhalation-exhalation cycle period.

In a preferred embodiment, upper end disc 10, cylindrical chamber 12, indicator disc 14, retainer 16, inhalation tube 18, first one-way valve 20, second one-way valve 22, and lower end disc 24 are constructed of a plastic material such as crystal polystyrene using injection molding techniques that are well known in the field. Preferably an ultra-sonic sealing process is used to join indicator disc 14 to retainer 16 and is also used to join upper end disc 10, cylindrical chamber 12 and lower end disc 24.

Having fully described my invention, it is to be understood that I do not wish to be limited to the details herein set forth, but my invention is of the full scope of the appended claims.

I claim:

1. An inhalation therapy device for encouraging prescribed breathing, by a patient, comprising:
   a moveable indicator responsive to patient inhalation flow rates;
   a chamber containing said indicator, said chamber including means for determining the position of said indicator within said chamber;
   first means for drawing patient inhalation gas from said chamber;
   second means to communicate to said chamber a volume of gas which is dependent upon a patient's inhalation flow rate with said indicator being adapted to float in said chamber upon and partially confine said volume of gas, said second means preventing gas flow from said chamber when patient inhalation gas flow ceases; and
   a flow passage through which said confined volume of gas flows after said patient gas flow ceases to reduce the volume of gas upon which said indicator floats thereby causing said indicator to sink in said chamber, said flow passage having varying cross-sectional flow area to cause said indicator to sink at a non-uniform rate whereby said flow passage and said confined volume of gas retards the sink of said indicator.

2. The device of claim 1 wherein the cross-sectional flow area of said flow passage varies in accordance with the position of said indicator in said chamber.

3. The device of claim 2 wherein the cross-sectional flow area of said flow passage increases as said indicator floats upwardly in said chamber and decreases as said indicator sinks downwardly in said chamber.

4. The device of claim 1, wherein said chamber includes a sidewall having an internal circular cross-section and said indicator includes an outer periphery spaced from said sidewall having a circular cross-section which is substantially coaxial with and smaller than said internal circular cross-section of said sidewall, said flow passage being defined by said sidewall and said indicator periphery.

5. The device of claim 4 wherein said device includes guide means for guiding said indicator axially with respect to said sidewall.

6. The device of claim 5 wherein said sidewall includes an upper and lower end and said internal circular cross-section is greater at one of said ends than said internal circular cross-section at said other end.

7. The device of claim 6 wherein said upper end has the greater internal circular cross-section.

8. The device of claim 5 wherein said sidewall includes an internal surface which is frusto-conical with respect to the longitudinal axis of said sidewall.

9. The device of claim 5 wherein said sidewall includes an upper internal surface which is frusto-conical with respect to the longitudinal axis of said sidewall and a lower internal surface which is cylindrical with respect to the longitudinal axis of said sidewall.

10. An inhalation device for indicating inhalation flow rate and time passage after inhalation, comprising:
    a vertical chamber having chamber sidewalls, a first and lower end, and second and upper end, said chamber sidewalls defining a first and lower chamber region with a substantially constant cross-sectional area, and further defining a second and upper chamber region with a varying cross-sectional area;
    an indicator member moveable within said vertical chamber and having a constant cross-sectional area slightly less than said first chamber region;
    means proximate said first end and in communication with said chamber for communicating patient inhalation gas into said chamber and for preventing gas flow from said chamber when patient inhalation ceases, said chamber sidewalls including a transparent portion for observing the position of said indicator within said chamber; and
    outlet means proximate said second end for drawing inhalation gas through said communicating means and said chamber, whereby said indicator floats in said chamber upon and partially confines said inhalation gas during said inhalation and said indicator sinks within said chamber after said inhalation ceases whereby a flow passage defined by said indicator and said chamber sidewalls allows said partially confined inhalation gas to escape to retard the sink of said indicator.

11. An inhalation device as in claim 10 wherein said varying cross-sectional area is a gradually increasing cross-sectional area from said first chamber region toward said second end.

12. An inhalation device as in claim 10 wherein said chamber sidewalls are tapered for providing said varying cross-sectional area.

13. An inhalation device as in claim 10, said device further includes one-way valve means in communication with said outlet means for providing an exhalation path that does not flow through said chamber.

14. An inhalation therapy device for encouraging prescribed breathing by a patient, comprising;
    a closed vertical chamber having a substantially cylindrical sidewall defining chamber cross-sectional area;
    an indicator disc having a circular periphery and a cross-sectional area slightly less than a portion of said chamber cross-sectional area, said chamber sidewall including at least a transparent portion for observing the position of said indicator within said chamber;
    a column member extending along the longitudinal axis of said chamber and about which said indicator disc is coaxially and moveably mounted for axial movement thereon with said periphery in spaced relation with respect to said sidewall;
    a gas inlet into said chamber to communicate patient inhalation gas to said chamber below said indicator disc and a gas outlet from said chamber above said indicator disc for drawing patient inhalation gas from said chamber;
    means for enabling said gas inlet to communicate said patient inhalation gas into said chamber to cause said disc indicator to float thereon upwardly and to partially confine said patient inhalation gas in said chamber and for preventing gas flow from said chamber when patient inhalation ceases; and
    a flow passage defined by said indicator disc periphery and said chamber sidewall through which said confined patient inhalation gas flows after said patient inhalation gas flow ceases to reduce the volume of gas upon which said indicator floats and thereby retard the sink of said indicator.

15. The device of claim 14 wherein the space between said indicator disc periphery and said chamber sidewall varies with respect to the position of said disc along at least a portion of said column.

16. The device of claim 15 wherein said sidewall includes an inside internal surface having a section which is frusto-conical and co-axial with said longitudinal axis of said chamber.

17. The device of claim 15 wherein said sidewall includes an upper internal surface which is frusto-conical with respect to said longitudinal axis of said chamber and a lower internal surface which is substantially cylindrical with respect to said longitudinal axis.

18. The device of claim 14 wherein said column member is hollow to define a gas passageway and said gas outlet from said chamber is in communication with said gas passageway.

19. The device of claim 18 wherein said device includes an inhalation passageway in communication with said gas passageway and said exhalation-inhalation passageway includes an exhalation outlet.

20. The device of claim 19 wherein means are provided to control said exhalation outlet whereby said exhalation outlet opens on exhalation and closes on inhalation.

21. The device of claim 20 wherein said means for enabling said gas inlet to communicate said patient inhalation gas into said chamber and said means to control said exhalation outlet each comprise a one-way valve.

22. An inhalation therapy device for encouraging prescribed breathing by a patient, comprising:
a closed chamber having sidewalls which define a first lower portion of said chamber having a first cross-sectional area and a second upper portion of said chamber having a second cross-sectional area, said second cross-sectional area being greater than said first cross-sectional area, said chamber having means for observing movement within said chamber;
a moveable indicator disposed within said chamber having a cross-sectional area slightly less than said first cross-sectional area, said device including means for guiding said indicator along a longitudinal axis of said chamber said indicator and said chamber sidewalls defining a flow passage having an area dependent upon the position of said indicator within said chamber;
outlet means for drawing patient inhalation gas from said chamber above said indicator; and
means for communicating gas into said chamber beneath said indicator when patient inhalation gas is drawn through said outlet means and for otherwise preventing gas flow from said chamber, whereby said indicator floats upon and partially contains a portion of said patient inhalation gas during patient inhalation to indicate inhalation flow rate and said indicator sinks as said partially contained gas flows through said flow passage to retard the sink of said indicator within said chamber once patient inhalation gas flow ceases.

23. An inhalation therapy device for encouraging prescribed breathing by a patient, comprising:
a chamber having an upper end and sidewalls which define a first lower portion of said chamber having a substantially constant cross-sectional area and a second upper portion of said chamber having a cross-sectional area increasing toward said upper end at a rate greater than any change in said substantially constant cross-sectional area;
a moveable indicator disposed within said chamber having a cross-sectional area slightly less than said substantially constant cross-sectional area, said indicator and said chamber sidewalls defining a flow passage having an area dependent upon the position of said indicator within said chamber;
outlet means for drawing patient inhalation gas from said chamber above said indicator; and
means for communicating gas into said chamber beneath said indicator when patient inhalation gas is drawn through said outlet means and for otherwise preventing gas flow from said chamber, whereby said indicator floats upon and partially contains a portion of said patient inhalation gas during patient inhalation to indicate inhalation flow rate and said partially contained inhalation gas flows through said flow passage to retard the sink of said indicator once patient inhalation gas flow ceases.

* * * * *